(12) United States Patent
Radentz

(10) Patent No.: US 8,658,227 B2
(45) Date of Patent: Feb. 25, 2014

(54) BOTANICAL FORMULATION DERIVED FROM BIRCH BARK

(76) Inventor: Leslie Marie Radentz, Temecula, CA (US)

( * ) Notice: Subject to any disclaimer, the term of this patent is extended or adjusted under 35 U.S.C. 154(b) by 128 days.

(21) Appl. No.: 12/932,703

(22) Filed: Mar. 2, 2011

(65) Prior Publication Data
US 2012/0223157 A1 Sep. 6, 2012

(51) Int. Cl.
*A61K 36/00* (2006.01)

(52) U.S. Cl.
USPC ............................ 424/769; 424/775; 424/725

(58) Field of Classification Search
None
See application file for complete search history.

(56) References Cited

U.S. PATENT DOCUMENTS

| | | | |
|---|---|---|---|
| 4,917,890 A | 4/1990 | McAnalley | |
| 5,750,578 A * | 5/1998 | Carlson et al. | 514/766 |
| 5,888,523 A * | 3/1999 | Galask et al. | 424/401 |
| 6,392,070 B1 | 5/2002 | Krasutsky et al. | |
| 6,572,868 B1 * | 6/2003 | Cope | 424/400 |
| 6,634,575 B2 | 10/2003 | Krasutsky et al. | |
| 6,768,016 B2 | 7/2004 | Krasutsky et al. | |
| 6,890,566 B2 * | 5/2005 | Arquette | 424/725 |
| 7,198,808 B2 | 4/2007 | Krasutsky et al. | |
| 2002/0155183 A1 * | 10/2002 | Bathurst et al. | 424/757 |
| 2004/0005369 A1 * | 1/2004 | Chuang et al. | 424/728 |
| 2004/0101503 A1 * | 5/2004 | Mahe et al. | 424/70.14 |
| 2008/0014162 A1 * | 1/2008 | Willemin et al. | 424/70.1 |
| 2008/0020996 A1 * | 1/2008 | Singh et al. | 514/59 |
| 2009/0068278 A1 * | 3/2009 | Golz-Berner et al. | 424/493 |
| 2009/0136566 A1 * | 5/2009 | Krasutsky et al. | 424/450 |
| 2009/0182158 A1 | 7/2009 | Krasutsky et al. | |
| 2010/0062086 A1 | 3/2010 | Dryet et al. | |
| 2011/0262552 A1 * | 10/2011 | Chamberland et al. | 424/547 |

FOREIGN PATENT DOCUMENTS

FR 2865400 A1 * 7/2005
KR 2009052088 A * 5/2009

OTHER PUBLICATIONS

Weckesser et al. Forsch Komplementmed. 2010. vol. 17, pp. 271-273.*

* cited by examiner

*Primary Examiner* — Chris R Tate
(74) *Attorney, Agent, or Firm* — Law Office of Owen J. Bates; Owen J. Bates

(57) ABSTRACT

A formulation and method of mitigation of symptoms of patients suffering from a neurocutaneous pain syndrome by topical application of the formulation. The formulation is obtained by steeping the bark of a tree from the genus *Betula* in an aqueous acidified solution and then subsequent filtering, packaging and sterilization.

13 Claims, No Drawings

BOTANICAL FORMULATION DERIVED FROM BIRCH BARK

BACKGROUND OF THE INVENTION

1. Field of the Invention

The present inventions deals with a botanical formulation made from the bark of a birch tree which can be used for the mitigation of conditions, diseases and disorders arising from, impacted by, or resulting in neurocutaneous malcircuitry.

2. Background

White Birch

White birch is a tree that is common to northern Europe and North America. It is known by its scientific name of *Betula pendula* or *Betula alba*. One of the chemicals isolated from birch bark is called betulin. Research suggests that betulin causes some types of tumor cells to start a process of self-destruction called apoptosis. Betulinic acid, which is made from betulin, has been studied as an anti-neoplastic agent. Betulinic acid has been reported to slow the growth of several types of tumor cells and may prove useful for treating several forms of cancer, including melanoma and certain brain cancers.

In 1994, scientists at the University of North Carolina reported that chemicals found in white birch bark slowed the growth of HIV. The following year, a researcher at the University of Illinois reported that betulinic acid killed melanoma cells in mice. Results from a German nonrandomized clinical trial published in 2006 indicated that birch bark extract may be an effective treatment for actinic keratosis, a pre-cancerous skin condition. Clinical trials are needed to determine what effect, if any, betulinic acid has in treating neoplastic disease in humans.

Some researchers think that birch bark has antimicrobial properties. For skin conditions, birch leaf tea has been used as a wash, and has been added to bath water. Birch bark and leaves have been applied directly to the skin without adverse effect. Birch oil is sometimes used in ointments or liniments and is considered a substitute for wintergreen. Birch bark is appreciated by cosmetic manufacturers for clearing the lumpy subcutaneous collections of fluid which appear as cellulite. Birch bark oil is marketed within the cosmetic industry for improving the cosmetic appearance of cellulite.

The bark, leaves, and buds from this and related birch trees are used in herbal and folk medicines on the skin to treat warts, eczema, and other skin conditions. The leaves are sometimes used on the scalp to help with hair loss and dandruff. Birch tar is used on the skin for skin irritations and parasites. Folk medicine advocates say that birch tea can be taken internally as a diuretic, mild sedative or as a treatment for rheumatism, gout, and kidney stones. Other claims for birch bark include the treatment of stomach problems, diarrhea, dysentery, and cholera. Native American Indians used birch bark for building canoes and for medicinal usage.

Some people drink fresh or bottled birch sap as a tonic. In Russia, birch bark has been consumed since 1834. In Europe, birch sap was fermented into beer, wine, and other spirits. The inner bark of birch was sometimes eaten as food. A sweetener, xylitol, is made from birch bark, and is safe for human consumption, even if diabetic. Birch bark tea can be made by steeping a teaspoon of the birch bark in a cup of boiling water for 15 minutes. Proponents recommend drinking from 2 to 5 cups of tea per day. Birch leaves are marketed for making teas. Birch bark flakes, powder, capsules, oil, sap, and liquid extracts are sold in herbal medicine shops and on the Internet. White birch bark is currently marketed as an FDA compliant nutritional supplement within the United States Plants, including birch trees, can inflict rashes and allergic symptoms upon susceptible individuals. Persons sensitive to aspirin are advised to avoid birch products, because birch is known to possess aspirin-like compounds; however, toothpicks made of birch bark are not known to be dangerous to aspirin sensitive individuals. Aspirin-like compounds may pose a hazard to patients with poor kidney function, internal bleeding and to persons taking blood thinners; however, no actual example of such a hazard, relevant to white birch bark, has ever been reported in the medical literature. Until clinical safety data is available, consumption of white birch bark should not be recommended to individuals for whom aspirin is contraindicated or to pregnant women, nursing women and children.

Neurocutaneous Malcircuitry

Neurocutaneous malcircuitry is defined and discussed herein as extraneous neural conduction and/or transmission, as evidenced by intense, expanding or relentless pain, paresthesias, pruritus, swelling, bruising or inflammation, dysfunction and/or neural reflexes precipitated by cytokines and/or accumulated neurotransmitters.

Neurocutaneous malcircuitry is evidenced by extraneous neural conduction and/or transmission. Extraneous neural conduction is clinically identified when neural pathways route neural transmission in a fashion inconsistent with normal anatomic neurophysiology. A clinical example of this is of a patient who reflexively tears when her nose is touched after an inflammatory insult to the nose. Aberrant neural pathways (malcircuitry) may be capable of misdirection, interference, propagation and amplification of normal neural signals. Intuitively, normal impulses, if aberrantly conducted to the wrong target, may feedback upon themselves through reflex arcs, amplifying sensory impulses. A possible clinical example of this abnormal sensory amplification is the hyperesthesia of erythromelalgia. Misdirected neural impulses may stimulate autonomic and somatic reflex arcs, thus propagating aberrant transmission and resulting in new aberrant transmissions. Extraneous neural transmission clinically occurs when neural transmissions occur independently of normal neural reception, stimulation, moderation, and/or extinction. An example of an extraneous neural transmission is the pain impulse generated by aberrantly sustained reflexive muscular contraction, even after the original impulse inciting the pain is long gone.

Empirically, accumulated cytokines and neurotransmitters are instrumental in the development of neurocutaneous malcircuitry. Cytokines are released in response to pain, injury, illness, and inflammation. Cytokines cause changes in membrane permeability and vascular flow, resulting in fluid congestion and impaired lymphatic drainage. Neurotransmitters would be expected to accumulate within the synaptic clefts of congested tissue, escaping the clearance which is normally facilitated by diffusion. Failure of neurotransmitter clearance from the synapse is known to result in abnormal persistence of neural signaling.

Complex regional pain disorders, (also known as causalgia and reflex sympathetic dystrophy), are often associated with a history of a persistent or intensely painful inciting event. Analysis of clinical observation suggests that when pain signals exceed a certain neuro-electric threshold, action potentials spill outside the neuron's normal path of saltatory conduction, forming an extraneous neural pathway along other conductive areas (like the stream formed by a river from a heavy rain). If this aberrant neural pathway (stream) closes a connective loop with a ganglionic reflex arc, it could be capable of relentlessly feeding back upon itself. Intuitively, when neural transmissions are misdirected to a neural reflex arc, a new sensory transmission may result from the reflex itself, resulting in an extraneous neural transmission and potentially expanding the neural malcircuitry.

It is well accepted that normal neural transmission may be misdirected by neural malcircuitry to the wrong target. Abnormal transmission may target any structure, function, or system of the body, depending upon the path of neural conduction. Inappropriate sweating, movement, vascular flow, or a host of other disruptions may ensue from neural transmission misdirected through extraneous neural circuits. For example, a female patient presented with a history of a laceration to the nasal sidewall from a motor vehicle accident years earlier. Ever since the laceration healed, light touch to her, still numb, nose resulted in intense pain of her cheek, with reflexive tearing from her right eye. One possible explanation is that cutaneous nerves were severed and inappropriately reconnected. However, the laceration did not physically include areas known to be innervated for the resulting sensation and reflexes (the right cheek, tear glands and tear duct are not "hard wired" from the nose).

It is unknown how neural cell bodies themselves may be incorporated in the abnormal conduction pathways of aberrant neural circuitry. But clinical examples of neurocutaneous malcircuitry demonstrate complete and instantaneous restoration of normal neural function when aberrant neural transmission is terminated. This suggests that normal nerve cell bodies are not harmed by participation within cytokine induced neural malcircuitry.

Neural Function Circuitry & Reflexes

Traditionally, neurotransmitters must be removed from the synapse for signal extinction. Signal extinction is accomplished at the neuromuscular junction by a) acetylcholinesterase which degrades and inactivates acetylcholine, b) cell uptake of the neurotransmitter; and c) simple diffusion.

The over-accumulation of the neurotransmitter, acetylcholine, within the synaptic cleft at the neuromuscular junction, results in failure of neural impulses to extinguish normally. A potentially lethal example of this is pesticide poisoning. Pesticides inactivate acetylcholinesterase, causing failure of enzymatic degradation of acetylcholine. Resultant over-accumulation of acetylcholine at the neuromuscular junction causes neural impulses to fail to extinguish normally. This results in sustained muscle contraction which freezes the muscles needed for vital functions.

It appears that neurotransmitters are not normally cleared from the neuromuscular junctions of patients suffering from conditions of neurocutaneous malcircuitry, but if acetylcholinesterase deficiency was the culprit, anti-cholinergic medications would be very helpful, yet they are not. Lack of neurotransmitter clearance by diffusion and/or cell uptake is likely culpable for extraneous neural transmissions, but there is more to this story. Aberrant neural reflexes of complex regional pain disorders, such as erythromelalgia, are known to progressively expand outside the region relevant to the inciting injury. Unbridled neural reflexes are to blame for much of the chaos of erythromelalgia. The brain is responsible for moderating normal reflexes, but fails to appropriately respond to the malcircuitry precipitated by inflammatory cytokine accumulation.

The peripheral nervous system receives sensory afferent signals from cutaneous nerves, and transmits these neural impulses to the spinal cord, where the signal is further transmitted to the brain. Reflexes work a little differently. Reflex impulses are routed through the dorsal root ganglion and into the spinal cord, where the nerve synapses with an efferent nerve and a motor transmission is automatically generated (ex: the knee jerk reflex when stretch receptors of the knee are stimulated). The brain, via the spinal cord, receives feedback relative to the stimulation of the stretch receptors, as well as to the dorsal horn's resultant muscular activity (the knee "jerk"). The brain processes the precise measure of inhibitory response required to moderate and extinguish the knee jerk reflex. The brain moderates reflexive response by inhibitory neural feedback transmitted through the descending inhibitory spinothalamic track (DIST). If the brain is damaged, hyper-reflexia may result due to inadequate inhibition of normal reflex arcs. For example, hyper-reflexia often results from the brain damage of hypertonic cerebral palsy. In contradistinction, normal inhibitory regulation of a healthy brain may fail to extinguish reflexes which have been altered by neurocutaneous malcircuitry.

The descending inhibitory spinothalamic track (DIST) is housed within the central nervous system, coursing from the brain through the spinal cord. Normally, neural reflex circuits between the peripheral nervous system and the DIST are subject to moderation and extinction by the brain. Clinically, the hyper-reflexia of neurocutaneous malcircuitry suggests that reflexes conducted along extraneous neural pathways are not well moderated by the DIST. In fact, neural transmission along cytokine induced neurocutaneous malcircuitry may actually incorporate the DIST, looping back and involving the brain in this messy malcircuitry. It is conceivable that cytokine induced neurocutaneous malcircuitry is involved in the manifestation of migraines, attention deficit disorder, autism, neuropsychiatric disease, and a host of other possible diseases.

BRIEF SUMMARY OF THE INVENTION

The present invention includes a topical formulation which is derived from the bark of a birch tree, preferably the bark of the *Betula alba* tree and a method of administering the formulation wherein treatment with the formulation and treatment results in mitigation of the signs and/or symptoms of a person experiencing conditions, diseases and/or disorders arising from, impacted by or resulting in neurocutaneous malcircuitry.

Examples of diseases arising from neurocutaneous malcircuitry include complex regional pain disorders and brachioradial pruritus. An example of a disease impacted by neurocutaneous malcircuitry is erythrotelangiectactic rosacea. Inflammatory cytokines are known mediators of rosacea. It is clinically obvious that sensory transmission is extraneously conducted to autonomic reflex arcs, resulting in intense red flushing when the patient's face is rubbed. An example of a disease resulting in neurocutaneous malcircuitry is arthritis. Inflammatory episodes of arthritis result in cytokine production responsible for extraneous neural pain transmission to muscular reflex arcs, resulting in sustained reflexive muscle contraction, stiffness, and loss of range of motion.

The present formulation has been clinically shown to mitigate extraneous neural transmission and conduction in hundreds of clinical subjects. The majority (over 90%) of clinical subjects suffering from refractory pain with frozen muscles, related to a past trauma or disease, demonstrated partial or complete cessation of persistent pain and restoration of range of motion within minutes of application of the inventive formulation. When applied to the skin, the inventive formulation rapidly clears clinical bruising, swelling, and inflammation. The solution terminates the clinical manifestations of extraneous neural transmission and promotes clearance of the neural malcircuitry.

Proposed Mechanism of Action of the Inventive Formulation

Without being limited to any specific explanation for the mitigating effects of the inventive formulation, a possible basis for its effect is described below which is based upon the generally accepted mechanism of neurocutaneous malcircuitry and the variety of clinical conditions which has been shown be improved and/or eliminated by the use of the inventive formulation Simply speaking, formulation of the invention breaks the "cytokine circuit", ending extraneous neural transmission and conduction. Without ongoing neural transmission, the abnormal circuitry is subject to clearance, facilitated by the lymphatic stimulation of the inventive formulation, terminating neural malcircuitry.

Birch bark is known to possess natural salicylates which are similar to aspirin; however, the known pharmacological effects of salicylates, betulin and betulinic acid don't account for the unique abilities of the present formulation to mitigate the symptoms of the various conditions described herein.

The inventor has observed rapid lymphatic emptying and clearance of edema when the inventive formulation has been applied to inflamed lymph nodes and swelling. Within minutes of topical application of the inventive formulation, indurated lymph nodes and tense tissue swelling become soft to palpation. It is possible that this same stimulation of lymphatic clearance is responsible for the cosmetic improvement of cellulite associated with birch bark.

The inventive formulation stimulates lymphatic flow and fluid clearance. As tissue fluid is cleared by stimulated lymphatic flow, the concentration gradient favors diffusion of accumulated neurotransmitters out of the synaptic cleft. Additionally, it is reasonable to deduce that stimulated lymphatics participate in the direct uptake of the accumulated cytokines. Removal of accumulated neurotransmitters from the synaptic cleft terminates extraneous neural transmissions at the synaptic junction. This premise is supported by the actual treatment history of a patient suffering from a painful frozen finger associated with arthritis pain. If accumulated neurotransmitters at the neuromuscular junction were responsible for the sustained contraction, then local clearance of those neurotransmitters would result in immediate restoration of range of motion. In fact, when the inventive formulation was applied to this patient's finger, the pain was immediately relieved, followed by restoration of complete range of motion within a matter of minutes.

Topical application of the inventive formulation disconnects the aberrant neurocutaneous transmission of even far reaching extraneous neural circuits interconnected to the skin. Old style Christmas lights are a good illustration of how this occurs; if one Christmas bulb is disconnected, the entire strand, as well as other connected strands, stop conducting electric current. Cessation of abnormal afferent transmission feeds back upon the spinothalamic track, resulting in immediate widespread analgesia and normalization of reflexes as the dysregulated reflexes are terminated. Clinical evidence suggests that when transmissions no longer flow through cytokine induced malcircuitry, the components of aberrant circuitry are subject to removal, which is facilitated by the lymphatic system. In contradistinction, cytokine induced malcircuitry does not appear to be removed by the body if the aberrant circuitry continues to flow with neuro-electric transmissions. The inventive formulation disrupts neurocutaneous malcircuitry, but could not be expected to cure any underlying pathological condition. Therefore, it is critical that any underlying inflammatory process has been adequately treated and extinguished. Ongoing inflammation, disease, and evolving injury may re-generate cytokines quickly enough to "replace the removed Christmas bulb" and maintain patency of the abnormal neural circuit.

Normal pain transmission is not blocked by the inventive formulation. The inventive formulation does not cause anesthesia. Discomfort related to the accumulation of inflammatory cytokines, often accompanying normal pain, may be soothed by the inventive formulation relevant to known anti-inflammatory properties of birch bark, but normal pain transmission and pain reflexes remain intact. Upon topical application of the inventive formulation, stimulated lymphatic flow diminishes swelling. Reduction of swelling reduces painful pressure on tissue nerve endings. Reduction of swelling also improves localized blood flow, potentially reducing anoxic pain related to vascular insufficiency or compartment syndrome. The inventive formulation mitigates extraneous neural transmission, swelling, bruising and inflammation, but does not block the transmission of normal sensation. This ability of the inventive formulation to mitigate pain related to neurocutaneous malcircuitry without blocking the sensation of normal pain has been shown in a numerous patients.

Neurocutaneous malcircuitry can recur if the underlying cause of the pain is not eliminated or if not adequately treated. While the inventive formulation offers adjunctive management options and utility for ongoing inflammatory conditions, the inventive formulation would not be expected to provide complete pain relief of extraneous neural transmission which would be continually arising from ongoing inflammatory conditions. Ongoing generation of extreme pain from an underlying untreated inflammatory condition (such as from an incarcerated femoral hernia) will not be blocked by the inventive formulation. As such, the safety profile of the inventive solution is much higher than of narcotics for attempting to manage abnormal pain. Narcotic analgesics are well known to mask the pain symptoms of a surgical emergency, resulting in diagnostic and treatment delay. Narcotics may also result in narcotic addiction, withdrawal, alterations in consciousness, coma and death. Vital neural transmissions and reflexes protect respiratory, cardiac, and other important functions. Narcotics cause central nervous system depression, interfering with vital brain transmissions for respiratory and cardiac drive. Narcotics also depress vital protective reflexes, such as the gag, cough, and blink reflexes. Although clinical experience with the inventive solution is largely restricted to less than 30 mls daily topical dosage, topical application of the inventive formulation has never blocked vital neural impulses or reflexes. Topical application of the inventive formulation in dosages greater than 30 mls per day has not been extensively tested and therefore is not recommended. After thousands of experimental applications, normal functional transmission has never demonstrated impairment by the inventive solution. The inventive solution is also safer than other alternative traditional medical treatments for abnormal pain. Non-steroidal anti-inflammatory drugs (NSAIDs) and steroids are known to pose multiple serious side effects and risks, including promotion of gastric ulcer formation and increasing the risk of life threatening internal hemorrhage. After over 700 clinical case studies, and thousands of experimental applications, no harmful side effects of the inventive solution have been identified.

In summary, the proposed explanation of the mechanism of the inventive formulation is that the topical application of the inventive formulation mitigates neural malcircuitry which is associated with cytokines and/or the accumulation of neurotransmitters, resulting in widespread normalization of any connected neural transmission and/or reflexes. By so doing, associated bruising, pain, swelling, paresthesia, muscle stiffness, and inflammation, as well as associated central, autonomic and/or somatic dysfunction is subject to normalization and/or relief.

DETAILED DESCRIPTION

Method of Making the Inventive Formulation

The general method of preparing the inventive formulation is to put ground birch bark (*Betula alba*) into an acidic solution, preferably an acetic acid solution, and allowing the birch bark to soak in the acidic solution for at least about 30 minutes. This step may optionally include any standard mechanical means of agitation. The concentration of acid in the solution is selected so that the final solution has a pH of between about 2 and about 5. The solution is then filtered to remove visible particulates. Optionally the birch bark/acid solution can be boiled for some or all of the soaking time.

The formulation is then placed into bottles, pump spray bottles or pressurized aerosol containers. The preferred option is to place the formulation into pump spray bottles because this provides for a convenient, cost effective and efficacious means of topical application. It also avoids the problem of contamination if the formulation is stored in a regular bottle and avoids the extra cost and possible side effects of propellants that are necessary for a pressurized aerosol container.

Optionally the inventive formulation may be mixed with medically acceptable or cosmetically/pharmaceutically/physiologically acceptable carriers, excipients, diluents, adjuvants, vehicles, preservatives, antibiotics and mixtures thereof appropriate for the formation of emulsions, slurries, poultices, drenches, balms, salves, pomades, oils, jellies, foams, creams, solutions, shampoos, soaps, lotions, ointment, hydrogels, bath gels, shower gels, and gels.

Preferred Method of Producing the Inventive Formulation

In a clean large stainless steel pot (or large Pyrex glass Erlenmeyer flask) between about 1,000 mg and about 10,000 mg (preferably about 4000 to about 5000 mg) of finely ground and dried *Betula alba* bark (Mountain Rose Herbs in Eugene, Oreg. 97405 phone: 1-800-879-9337) is combined with distilled water and glacial acetic acid such that the proportion of acetic acid to water produces a pH in the range of about 3.0 to 4.0 with a total volume of liquid of about 400 mls. Subsequent steps are described below.

An alternative procedure is to mix 59 milliliters distilled white vinegar (which is about 5% acetic acid) with finely ground and dried *Betula alba* bark (from Mountain Rose Herbs) in the weight range of between 1,000 mg and 10,000 mg (preferably between about 4000 to about 5000 mg). Stir with a stainless steel whisk which is inserted into a stainless steel automatic stirring apparatus, and place on a heating element. Stir until the liquid comes to a boil. Distilled water in the amount of 355 mls is then added, stirring is continued and the contents brought back to a boil for no less than 30 minutes, but for no more than about one hour while the heat level was observed and adjusted to avoid boiling over of the liquid. The solution was removed from the heating element and the pot is covered with a clean stainless steel lid (a clean glass stopper or clean paper towel may be substituted as a lid if a flask is used) and allowed to sit undisturbed for at least 60 minutes.

Specifically, the initial extract of Birch bark can be achieved by boiling and/or soaking in vinegar (about 5% acetic acid) and then diluting the vinegar by the addition of water or in the alternative all of the boiling and/or soaking is done in the diluted vinegar.

The contents of the flask was filtered such that printed material of Arial bold characters with a font size 40 or smaller can be read through one inch depth of solution under the bottom of a clear glass beaker. Two means of achieving this level of clarity have been utilized, though there are many other means well known in the art.

One method is to filter through a filter funnel with three layers of filter paper of 5 micron of less pore size and repeating this filtration twice more with the filtered solution, through fresh 3 ply paper filters (or an equivalent filtration medium). The alternative is to perform three successive vacuum filtrations thorough membrane filters having a pore size of about 5 microns or less. Optimal product color is a pale golden yellow and has a pH of about 3 to 4.

The solution is funneled into a glass bottle, labeled and assembled with fine mist aerosol pump, and then plastic shrink wrap was applied to protect the bottle from tampering and contamination. The packaged bottles is then subjected to gamma irradiation for a calculated period of time, dependent upon the weight of the solution, to achieve a specific calculate dose of irradiation delivered of at least about 30 kGy, but no more than about 50 kGy.

EXAMPLES

Over 700 patients have been treated with the inventive formulation while under the care of the inventor, a California licensed medical doctor, specialized in dermatology. The majority of patients were suffering with conditions which arose from, were impacted by or resulted in neurocutaneous malcircuitry, and which had failed standard medical treatments before receiving a topical application of the inventive solution. The only treatment failures were associated with ongoing inflammatory disorders such as an incarcerated femoral hernia, osteomyelitis, and bone fracture non-union. A more complete understanding of the present invention can be obtained by reference to the following specific examples. The examples are described solely for purposes of illustration and are not intended to limit the scope of the invention. The symptoms of patients suffering from conditions of neurocutaneous malcircuitry were mitigated by the inventive formulation as evidenced by the ratings of clinical patients regarding improvement of acute and chronic pain, as well as subject reports of normalization of function, sensation, numbness, and pruritus. Medical conditions mitigated by the inventive formulation include normalization of signs, symptoms, functions, control, and/or conditions impacted by neural maltransmission and/or malcircuitry including, but not limited to, the following examples of the documented clinical effects on patients suffering from the clinical conditions listed below:

1. Normalization of muscle tone, range of motion, and muscular control (resolution of inappropriate muscle contractions in cases of arthritis and radiculopathy complicated by clinical evidence of neurocutaneous malcircuitry).

2. Reduction of abnormal involuntary somatic movement (reduction of involuntary movement in cases of benign essential tremor, hemispasms, and tardive dyskinesia impacted by neurocutaneous malcircuitry).

3. Reduction of abnormal autonomic activity (reduction of flushing impacted by cytokine induced neurocutaneous malcircuitry of rosacea).

4. Reduction of abnormal vascular flow (resolution of burning feet syndrome hyperemia due to neurocutaneous malcircuitry of erythromelalgia).

5. Reduction of abnormal inflammation (reduction of redness, swelling and pain from carpet burn, spider bite, drug induced dermatitis, radiation dermatitis, hypersensitivity reactions types II-IV, post surgical tissue changes, acne, seborrheic dermatitis).

6. Reduction of hyperhidrosis (resolution of sweaty macerated feet arising from neurocutaneous malcircuitry with sympathetic stimulation of erythromelalgia).

7. Reduction of normal and abnormal bruising and swelling (reduction of and hastened resolution of post traumatic and spontaneous bruising related to trauma, vascular stasis, liposuction, Coumadin, and excision of skin cancers).

8. Reduction of abnormal secretory and ductal dysfunction (resolution of abnormal reflexive tearing sustained by facial trauma induced neurocutaneous malcircuitry)

9. Normalization of bladder control and function (complete resolution of neurogenic bladder associated with the neurocutaneous malcircuitry of erythromelalgia)

10. Reduction of hyperesthesia, inflammation and pain escalation of normal acute, chronic pain, and from infection (analgesia related to disruption of extraneous neural transmission and conduction of trigeminal neuralgia, post herpetic neuralgia, MRSA infection of skin, burn pain, injuries, arthritis)

Example #1

Erythromelalgia

One of the first patients treated with the formulation of the invention suffered from Erythromelalgia, which is one of the conditions resulting from neurocutaneous malcircuitry. Erythromelalgia results in radiating progressive pain associated with autonomic system dysregulation. The pain and neural malcircuitry of erythromelalgia typically extends to the feet, and this pain is refractory to all medical and surgical treatment modalities. Typically the skin of the feet in erythromelalgia, is very inflamed, hot, and red in color, and is associated with severe recalcitrant pain. On May 16, 2006, an elderly white female, suffering with erythromelalgia, sought assistance from the treating physician and asked if there was anything that could be done to help her with her excruciating pain. Historically, the patient had suffered from multiple rheumatologic and orthopedic problems, associated with chronic severe back pain. Over many years, multiple spinal surgeries failed to correct her upper and lower back pain, and she became unable to walk normally or lift her arms over her head. She then developed a neurogenic bladder and became unable to void without manually pushing her bladder to obtain urinary flow. In 2001, the patient began to suffer intense feet pain, associated with heat and color changes. The only relief that she could get was from standing in a tub of ice water, and this relief was only temporary. Her erythromelalgia was refractory to additional neurosurgical efforts, pain medications, physical therapy and nerve blocks. When she was examined, the patient was unable to ambulate normally, dragging one leg as she walked and she ambulated with a very stooped posture. She also demonstrated that she could not lift her arms above her shoulders. The patient's feet were very warm, sweaty and reddened in color bilaterally.

After obtaining informed consent to participate in Clinical Case Study Research, the inventive formulation was applied to the most painful foot. It was observed that the redness of the foot disappeared within seconds. The patient exclaimed that the foot pain, as well as much of her lower back pain was immediately relieved by this application, even though the formulation had only been applied to that one foot. While observing her response to application of the inventive formulation to the one foot, the redness of the contra lateral foot immediately disappeared. The patient's posture spontaneously straightened from the formerly hunched posture. The patient was now smiling and laughing excitedly. She reached down and touched her toes, demonstrating a range of motion that she had not experienced in years. The inventive formulation was then applied directly over the local orthopedic tenderness sites of the upper and lower back. The patient instantly raised her arms above her head, rejoiced and began to demonstrate restoration of full range of movement of the upper extremities. The patient ambulated normally from the clinic with erect and normal posture and was no longer dragging her leg. A few hours later that day, she called from her home to report that she was now able to spontaneously and normally empty her bladder, for the first time in many years. Application of the inventive formulation to the skin regions associated with the patient's neural malcircuitry resulted in spontaneous remission of her neurogenic bladder. The patient reported that she remained pain free with continued normalization of bladder and ambulatory functions on the following day. She was advised to continue to apply the inventive formulation twice daily, but she discontinued regular application of the inventive formulation after a few days because she was no longer symptomatic of her erythromelalgia. This patient remained free of her erythromelalgia and neurogenic bladder over five years later, and has sustained this improvement until this writing. She occasionally applies the inventive formulation to control the pain and stiffness of her chronic arthritis in her shoulders and spine. She still no longer requires a cane for ambulation.

Example #2

Herpes Zoster Infection and Post Operative Pain

An elderly white male with an active herpes zoster Infection was examined and found to be suffering from pain characterized as 15/10 on a pain scale of 1-10. Narcotics, steroids, capsaicin cream, and antiviral medication failed to relieve his pain. After obtaining informed consent for participation in Clinical Case Study Research, the inventive formulation was applied over the involved dermatome. Pain relief was obtained upon application, and the patient was advised to apply the inventive formulation at home twice daily. The patient states that the inventive formulation provided the only successful pain relief during his zoster infection. Application of the inventive formulation allowed the patient to finally be able to sleep at night, and the baseline pain gradually decreased with ongoing usage. After several weeks, the patient was free of zoster pain, and he discontinued application of the inventive formulation. He continued to maintain relief from the zoster pain during the subsequent two years, even without further application of the inventive formulation.

This same patient later suffered from post operative orthopedic pain and stiffness in his shoulders. He was unable to obtain adequate relief with narcotics and other traditional medications. He characterized the pain as 8/10 when he tried to lift his right arm. Within a minute of topical application of the inventive formulation, his pain was reduced to 2/10, and he obtained greater range of motion.

Example #3

Brachioradial Pruritus

A middle aged white female was examined found to have constant and severe pruritus over the posterio-lateral bilateral arms. Her diagnosis was brachioradial pruritus. She had suffered with this disorder for many years and her condition had been unsuccessfully treated with scabicide cream, steroids, and antihistamines. The only relief that she could obtain was to apply ice to her arms. Although the pruritus was constant, her worst pruritus was at night, which disrupted her sleep. After obtaining informed consent to participate in Clinical Case Study Research, the inventive formulation was applied to the involved areas, and complete symptomatic relief of pruritus was obtained within minutes. She continued to apply the inventive formulation to the involved areas at home once daily, before bedtime. The pruritus episodes became less frequent. She discontinued daily application of the inventive formulation, using the product only when she became symptomatic. Upon clinical follow up, a few months later, the patient estimated that frequency of the pruritus was reduced to only about twice a month.

Example #4

Facial Twitching (Facial Hemispasm)

A 71 year old white female was examined on Feb. 3, 2010 with severe disfiguring facial drooping after receiving botox for right facial hemispasms (severe twitching). The patient was very unhappy with the disfiguring results of the botox treatment administered by her neurologist. Her facial spasms returned 3 after her botox injection. On Sep. 22, 2011, she was examined and found to have right eye eyelid, right cheek, right perioral, and right platysmal muscle twitching, which was very distracting when she tried to engage in communication. After obtaining informed consent to participate in Clinical Case Study Research, she was allowed to apply the inventive formulation to the involved facial regions. She was examined again on Jan. 25, 2011 with improvement of the intensity and frequency of the facial spasms. It was noted that light touch on a post auricular region of the neck resulted in reflexive spasms. In this case, Intense Pulsed light was applied this trigger point of reflexive spasms, with no benefit noted. The patient was advised to apply the inventive formulation to the involved region, including the trigger point, every four hours while awake. The next morning, the patient awoke with no spasms, and her result was sustained for the next four days, the patient was completely free of her facial hemispasms; however, the patient discontinued use of the inventive formulation when the facial hemispasms disappeared. The hemispasms began to recur on the fifth day after the last application of the inventive formulation. Upon resumption of daily application of the inventive formulation, the hemispasms were again diminished.

Example #5

Vulvodynia

A 30 year old white female was examined and complained of severe episodic genital region pain. The condition began during a long overseas flight to Australia. She experienced extreme pain when sitting. The most painful tissue, at the posterior aspect of the vaginal extroitus, was observed to become very red, swollen and macerated during pain episodes. Antidepressants, pain medications, and steroid creams were tried and proved unsuccessful in managing the pain. Her condition became complicated by pruritus, possibly due to steroid-related dermatitis. Even during pain free intervals, any manipulation of the involved region resulted in swelling and pain. The painful site was biopsied by her gynecologist, and histopathologic examination revealed no pathology. She was diagnosed with vulvodynia, but did not obtain effective treatment. The patient sought help from many medical specialists, only to be misdiagnosed as having a psychosomatic disorder. She was examined by the inventor several months before her scheduled wedding. Upon examination, there was evidence of a prior biopsy scar at the vaginal extroitus. There was no exudate, sclerosis, or lymphadenopathy. Given the history, the patient was diagnosed with vulvodynia related to angioedema complicated by steroid dermatitis. After obtaining informed consent to participate in Clinical Case Study the inventive formulation was applied to the involved region. The patient obtained immediate symptomatic relief of pain after application of the inventive formulation. Topical steroids were discontinued and the patient was instructed to apply the inventive formulation twice daily and as needed. She was also instructed to avoid long periods of sitting and to avoid long overseas air travel. Her painful episodes became less frequent and less intense. Her marriage was consummated in November of 2010. Although the inventive solution did not cure the tendency toward angioedema underlying her vulvodynia, the invention allowed her to enjoy comfortable sexual relations and provided effective symptomatic management of her condition.

Clinical Case Study #6

Post Surgical, Arthritis, and Bone Fracture Pain

On Feb. 14, 2011, a middle aged white female was examined and found have pain at a level of 4-5 out of 10 (10 being the worst pain) of her neck related to plastic surgery procedures that had been performed within the prior few weeks. She also complained of 4 out of 10 pain in her right hip from arthritis, and 4-6 out of 10 pain from orthopedic surgery related to a fracture of her left foot. After obtaining informed consent to participate in Clinical Case Study Research, the inventive formulation was applied to the involved regions. The Subject obtained complete relief of each of these pain conditions within a few minutes after topical application of the Solution. She rated her pain as zero (no pain) within 5 minutes of each application.

Case Study #7

Bullous Pemphigoid of the Breast Folds and 5-Fluorouracil Dermatitis of the Neck An elderly female developed a new onset itchy and painful eruption within her inferior breast folds which appeared following the eruption of a painful dermatitis on her neck. Both eruptions were refractory to topical steroids prescribed by her primary care physician. The neck eruption was well demarcated to the area of 5-fluorouracil cream application for actinic keratosis, consistent with drug induced dermatitis. The breast fold eruption was thought to be caused by severe yeast dermatitis with secondary bullous impetigo; thus, empiric antibiotic and topical antifungal therapy was begun. Bacterial cultures returned negative. This eruption failed to clear after empiric antimicrobial therapy. The eruption was biopsied. Histological tissue examination demonstrated many eosinophils and a subepidermal split diagnostic of bullous pemphigoid. The bullous lesions and macerated psoriasiform patches were localized only to the region of the inferior breast folds, consistent with the vegetative form of Bullous Pemphigoid. The vegetative form of bullous pemphigoid has a predilection for the intertriginous areas of the skin. It is unclear whether the 5-fluorouracil treatment may have precipitated this case of bullous pemphigoid.

After obtaining informed consent to participate in Clinical Case Study Research, the inventive formulation was applied to both the neck and breast fold eruptions. The patient immediately obtained symptomatic relief of the pain and itchiness of both the neck and breast fold eruptions. She was advised to apply the solution twice daily at home. At her one week follow up, the inflammatory eruption of the neck had completely cleared and the breast fold pain and itchiness had ceased. The inflammation and induration of the breast fold eruption had also improved; however, bullous lesions continued to erupt. Once the histologic diagnosis of bullous pemphigoid was obtained, traditional treatment with tetracycline was begun, and the patient continued application of the inventive formulation twice daily. Although the inventive formulation had not cleared all of the eruption associated with the bullous pemphigoid, she obtained complete symptomatic relief of the pain and itchiness with the inventive formulation.

Example #8

Erythema Nodosum

On Nov. 2, 2010, a female college student was examined and found to have painful subcutaneous nodules of erythema nodosum which arose after resolution of mononucleosis. The nodules were distributed over the bilateral lower extremities and were very tender after she had been on her feet for a while. The pain and induration of the nodules were refractory to diphenhydramine and NSAID medication. After obtaining informed consent to participate in Clinical Case Study Research, the inventive formulation was applied to the involved regions. Pain was immediately relieved and the nodules became softer and smaller in size within minutes. Support stockings were recommended, along with daily application of the inventive formulation. The patient obtained excellent symptomatic management of her erythema nodosum. The condition was no longer apparent a few weeks later at clinical follow up.

Example #9

Imiquimod Induced Dermatitis Complicated by Methicillin Resistant *Staphylococcus Aureus*

On Apr. 29, 2008, a 74 year old white female was examined and found to have a very painful, swollen, fissured nose with copious exudate. The eruption began after application of imiquimod to the nose to treat actinic keratosis. A culture was performed. After informed consent to participate in Clinical Case Research, the inventive formulation was applied to the entire nasal eruption. The patient experienced relief of pain and swelling upon application of the inventive formulation. She was advised to discontinue the imiquimod and to apply the inventive formulation to the nasal eruption twice daily. Empiric antibiotic treatment was initiated. Culture results returned positive for Methicillin Resistant *Staphylococcus aureus*. The bacterial sensitivity demonstrated that the *Staphylococcus aureus* was sensitive to the prescribed antibiotic. Upon clinical follow up, on Jun. 19, 2008, the infection had cleared and the nose was well healed without scarring, pain or discomfort. No recurrence of the actinic keratosis was evident upon later follow up of Feb. 15, 2011. The cosmetic result was excellent as evidenced by smooth texture and normal coloration at the actinic keratosis treatment site.

Example #10

Pain with Neurocutaneous Malcircuitry Resulting in Restricted Range of Motion

An elderly white female was examined for a skin condition. She mentioned that she was in severe pain from arthritis of the right shoulder. She reported that her other doctor diagnosed her with arthritis of the right shoulder. The shoulder pain was refractory to NSAID medications. The patient found physical therapy to be painful and of questionable benefit. She was not able to lift her right arm above her shoulder, and movement of the shoulder was very painful (9+ out of 10 on the pain scale). After informed consent was obtained to participate in Clinical Case Research, the inventive formulation was applied to the right shoulder. Three months later, the patient returned for follow up on her skin condition and reported that she had obtained 100% sustained pain relief and restoration of complete range of motion of the right shoulder since that one time office application of the inventive formulation.

Example #11

Post Traumatic Hyperesthesia, Numbness and Dysreflexia

A young adult female sustained a laceration to the nasal side wall from a motor vehicle accident several years prior to clinical presentation. Ever since the nasal laceration healed, a light touch to her nose (which remained numb since the accident) resulted in intense pain of her cheek, associated with reflexive tearing from her right eye (and not her left). After obtaining informed consent to participate in Clinical Case Study Research, the inventive formulation was applied to the involved regions. After topical application of the inventive formulation, the numbness, reflexive pain, and reflexive tearing were instantly extinguished and normal sensation was restored to her nose. Upon clinical follow up, years later, there was no recurrence of the pain, numbness, or abnormal reflexive tearing. Resolution of the extraneous neural conduction and transmission was sustained since that one single application of the inventive solution.

Example #12

Spider Bite

An elderly white female when examiner was found to be suffering with excruciating pain of several days duration associated with an expanding and ulcerating lesion over the right medial thigh. She was afebrile. There was no purulent drainage, no crusting, and no honey colored exudate associated with the lesion. The pain was refractory to the antibiotics and traditional pain medications prescribed by her regular doctor. Black widow spiders are common to the Southern California region in which the patient lived. Given the intensity of the pain and lack of evidence for infection, she was diagnosed with black widow spider bite. After obtaining informed consent to participate in Clinical Case Study Research, the inventive formulation was applied to the site of the lesion and pain relief was obtained within seconds. The patient applied the inventive solution twice daily for two to three weeks until the lesion was completely healed, and during this time the solution effectively managed her pain. The lesion promptly regressed and healed in response to the inventor's formulation. There was no residual pain, numbness or paresthesia upon clinical follow up.

Although the preferred embodiments of the present invention have been disclosed for illustrative purposes, those skilled in the art will appreciate that various modification, additions and substitutions are possible, without departing from the scope and spirit of the invention.

I claim:

1. A method for treating a human subject suffering from a condition arising from, impacted by or resulting in neurocutaneous malcircuitry, comprising the step of topically administering a formulation comprising an effective amount of an aqueous acidic extract of the bark of a tree from the genus *Betula* to the human subject.

2. The method of claim 1 wherein the tree is from the species *Betula alba*.

3. The method of claim 2 wherein the pH of the formulation is between about 2.0 and about 5.0.

4. The method claim 3 wherein the formulation comprises acetic acid.

5. The method of claim 4 wherein the formulation has been filtered one or more times.

6. The method of claim 5 wherein the filter has a pore size equal to or less than but 5.0 microns.

7. The method of claim 6 wherein the formulation is subjected to 30-50 kGY of gamma radiation after the formulation has been filtered.

8. The method of claim 7 wherein the formulation has been subjected to gamma radiation for a calculated period of time, dependent upon batch weight, to achieve a specific calculated dose of irradiation delivered of at least about 30 kGy, but no more than about 50 kGY, after the formulation has been filtered.

9. The method of claim 8 wherein the formulation is packaged in a pump spray container.

10. The method of claim 1 wherein the topical application of the formulation does not block vital neural transmissions or reflexes.

11. The method of claim 6 wherein the formulation further comprises one or more medically acceptable or cosmetically/pharmaceutically/physiologically acceptable excipients selected from the group consisting of carriers, diluents, adjuvants, vehicles, preservatives, antibiotics and mixtures thereof.

12. The method of claim 11 wherein the formulation is in a form selected from the group consisting of emulsions, slurries, poultices, drenches, balms, salves, pomades, oils, jellies, foams, creams, solutions, shampoos, soaps, lotions, ointment, hydrogels, bath gels, shower gels, and gels.

13. A method for treating a human subject suffering from a condition arising from, impacted by or resulting in neurocutaneous malcircuitry, comprising the step of topically administering an effective amount of a formulation consisting essentially of an aqueous acidic extract of the bark of a tree from the genus *Betula* to the human subject.

* * * * *